US010316034B2

(12) United States Patent
Savory et al.

(10) Patent No.: US 10,316,034 B2
(45) Date of Patent: Jun. 11, 2019

(54) PHARMACEUTICAL SALT FORMS OF AN INHIBITOR OF SEMICARBAZIDE-SENSITIVE AMINE OXIDASE (SSAO)

(71) Applicant: BENEVOLENTAI CAMBRIDGE LIMITED, London (GB)

(72) Inventors: Edward Savory, Cambridge (GB); Michael Higginbottom, Cambridge (GB)

(73) Assignee: BENEVOLENTAI CAMBRIDGE LIMITED, London (GB)

( * ) Notice: Subject to any disclaimer, the term of this patent is extended or adjusted under 35 U.S.C. 154(b) by 0 days.

(21) Appl. No.: 15/567,536

(22) PCT Filed: Apr. 22, 2016

(86) PCT No.: PCT/GB2016/051119
§ 371 (c)(1),
(2) Date: Oct. 18, 2017

(87) PCT Pub. No.: WO2016/170351
PCT Pub. Date: Oct. 27, 2016

(65) Prior Publication Data
US 2018/0111928 A1 Apr. 26, 2018

(30) Foreign Application Priority Data

Apr. 24, 2015 (GB) .................................. 1507031.1

(51) Int. Cl.
C07D 471/04 (2006.01)
A61P 27/02 (2006.01)
A61P 17/06 (2006.01)
A61P 37/02 (2006.01)
A61P 9/10 (2006.01)
A61P 25/28 (2006.01)
A61P 31/00 (2006.01)
A61P 37/08 (2006.01)
A61P 7/12 (2006.01)
A61P 9/04 (2006.01)
A61P 25/08 (2006.01)
A61P 25/16 (2006.01)
A61P 29/00 (2006.01)
A61P 17/04 (2006.01)

(52) U.S. Cl.
CPC .............. *C07D 471/04* (2013.01); *A61P 7/12* (2018.01); *A61P 9/04* (2018.01); *A61P 9/10* (2018.01); *A61P 17/04* (2018.01); *A61P 17/06* (2018.01); *A61P 25/08* (2018.01); *A61P 25/16* (2018.01); *A61P 25/28* (2018.01); *A61P 27/02* (2018.01); *A61P 29/00* (2018.01); *A61P 31/00* (2018.01); *A61P 37/02* (2018.01); *A61P 37/08* (2018.01)

(58) Field of Classification Search
CPC ..................................................... C07D 471/04
USPC ......................................................... 514/303
See application file for complete search history.

(56) References Cited

U.S. PATENT DOCUMENTS

| 4,141,899 A | 2/1979 | Arcari et al. |
|---|---|---|
| 4,223,146 A | 9/1980 | Arcari et al. |
| 6,908,926 B1 | 6/2005 | Doerwald et al. |
| 8,263,616 B2 * | 9/2012 | Savory ................. A61K 31/437 514/303 |
| 2002/0198189 A1 | 12/2002 | Besencon et al. |
| 2007/0066646 A1 | 3/2007 | Clauzel et al. |
| 2018/0085357 A1 | 3/2018 | Savory |

FOREIGN PATENT DOCUMENTS

| WO | 02/038153 A1 | 5/2002 | |
|---|---|---|---|
| WO | 2007/146188 | 12/2007 | |
| WO | 2010/031789 | 3/2010 | |
| WO | WO 2010/031789 | * 3/2010 | ........... C07D 471/04 |
| WO | 2014/199171 | 12/2014 | |
| WO | 2015/159112 | 10/2015 | |

OTHER PUBLICATIONS

Brittain:Developing an Appropriate Salt Form for an Active Pharmaceutical Ingredient | American Pharmaceutical Review—The Review of American Pharmaceutical Business & Technology, American Pharmaceutical Review, 2009.*
Bauer: Pharmaceutical Solids—The Amorphous Phase, J. of Validation Technology, 15, 3, 63-6, 2009.*
Wermuth, Handbook of Pharmaceutical Salts passsage, Jan. 1, 2002, Hand bood of pharmaceutical salts. Properties selection and use, pp. 1-7.*
Nakos et al., "Light Microscopic Visualization of Semicarbazide-Sensitive Amine Oxidase (Benzylamine Oxidase) Using a Cerium Method", *Folia Histochemica et Cytobiologica*, vol. 32, No. 1, pp. 3-10, 1994.
Lyles et al., "Properties and Functions of Tissue-bound Semicarbazide-Sensitive Amine Oxidases in Isolated Cell Preparations and Cell Cultures", *J. Neural. Transm. Suppl.*, vol. 52, pp. 239-250, 1998.
Castillo et al., "Semicarbazide-Sensitive Amine Oxidase (SSAO) from Human and Bovine Cerebrovascular Tissues: Biochemical and Immunohistological Characterization", *Neurochemistry International*, vol. 33, pp. 415-423, 1998.
Jaakkola et al., "Human Vascular Adhesion Protein-1 in Smooth Muscle Cells", *American Journal of Pathology*, vol. 155, pp. 1953-1965, 1999.
Kurkijärvi et al., "Circulating Form of Human Vascular Adhesion Protein-1 (VAP-1): Increased Serum Levels in Inflammatory Liver Diseases", *J. Immunol*, vol. 161, pp. 1549-1557, 1998.
Enrique-Tarancón et al., "Role of Semicarbazide-Sensitive Amine Oxidase on Glucose Transport and GLUT4 Recruitment to the Cell Surface in Adipose Cells", *J. Biol. Chem.*, vol. 273, pp. 8025-8032, 1998.

(Continued)

*Primary Examiner* — Nizal S Chandrakumar
(74) *Attorney, Agent, or Firm* — Greenblum & Bernstein, P.L.C.

(57) ABSTRACT

The mesylate and sulphate salts of (3S)-Tetrahydrofuran-3-yl (4S)-4-isopropyl-,4,6,7-tetrahydro-5H-imidazo[4,5-c]pyridine-5-carboxylate mesylate, and hydrates thereof, and their use in medicine.

8 Claims, 2 Drawing Sheets

(56) References Cited

OTHER PUBLICATIONS

Mercier et al., "Semicarbazide-Sensitive Amine Oxidase Activation Promotes Adipose Conversion of 3T3-L1 cells", *Biochem. J.*, vol. 358, pp. 335-342, 2001.
Fontana et al., "Amine Oxidase Substrates Mimic Several of the Insulin Effects on Adipocyte Differentiation in 3T3 F442A Cells", *Biochem. J.*, vol. 356, pp. 769-777, 2001.
Salmi et al., "Vascular Adhesion protein-1 (VAP-1)", *Adhesion Molecules: Function and Inhibition*, edited by Klaus Ley, pp. 237-251, 2007.
Langford et al., "Semicarbazide-Sensitive Amine Oxidase and Extracellular Matrix Deposition by Smooth-Muscle Cells", *Cardiovascular Toxicology*, vol. 2, pp. 141-150, 2002.
Göktürk et al., "Overexpression of Semicarbazide-Sensitive Amine Oxidase in Smooth Muscle Cells Leads to an Abnormal Structure of the Aortic Elastic Laminas", *Am. J. Pathol.*, vol. 163, No. 5, pp. 1921-1928, 2003.
Boomsma et al., "Plasma Semicarbazide-Sensitive Amine Oxidase is Elevated in Patients with Congestive Heart Failure", *Cardovascular Research*, vol. 33, pp. 387-391, 1997.
Boomsma et al., "Circulating Semicarbazide-Sensitive Amine Oxidase is Raised Both in Type I (Insulin-Dependent), in Type II (Non-Insulin-Dependent) Diabetes Mellitus and Even in Childhood Type I Diabetes at First Clinical Diagnosis", *Diabetologia*, vol. 42, pp. 233-237, 1999.
Mészáros et al., " Determination of Human Semm Semicarbazide-Sensitive Amine Oxidase Activity: A Possible Clinical Marker of Atherosclerosis", *European Journal of Drug and Metabolism and Pharmacokinetics*, vol. 24, No. 4, pp. 299-302, 1999.
Mátyus et al., "Semicarbazide-Sensitive Amine Oxidase: Current Status and Perspectives", *Current Medicinal Chemistry*, vol. 11, pp. 1285-1298, 2004.
Del Mar Hernandez et al., "Human Plasma Semicarbazide Sensitive Amine Oxidase (SSAO), β-Amyloid Protein and Aging", *Neuroscience Letters*, vol. 384, pp. 183-187, 2005.
O'Sullivan et al., "Semicarbazide-Sensitive Amine Oxidases: Enzymes with Quite a Lot to Do", *NeuroToxicology*, vol. 25, pp. 303-315, 2004.
Callingham et al., "Some Aspects of the Pathophysiology of Semicarbazide-Sensitive Amine Oxidase Enzymes", *Progress in Brain Research*, vol. 106, pp. 305-321, 1995.
Jiang et al., "The Contribution of Cerebral Vascular Semicarbazide-Sensitive Amine Oxidase to Cerebral Amyloid Angiopathy in Alzheimer's Disease", *Neuropathology and Applied Neurobiology*, vol. 34, pp. 194-204, 2008.
Salmi et al., "A Cell Surface Amine Oxidase Directly Controls Lymphocyte Migration", *Immunity*, vol. 14, pp. 265-276, 2001.
O'Rourke et al., "Benefit of Inhibiting SSAO in Relapsing Experimental Autoimmune Encephalomyelitis", *J. Neural Transm.*, vol. 114, pp. 845-849, 2007.
Stolen et al., "Absence of the Endothelial Oxidase AOC3 Leads to Abnormal Leukocyte Traffic In Vivo", *Immunity*, vol. 22, pp. 105-115, 2005.
Kirton et al., "Function-Blocking Antibodies to Human Vascular Adhesion Protein-1: A Potential Anti-Inflammatory Therapy", *Eur. J Immunol.*, vol. 35, pp. 3119-3130, 2005.
Salter-Cid et al., "Anti-Inflanunatory Effects of Inhibiting the Amine Oxidase Activity of Semicarbazide-Sensitive Amine Oxidase", *J. Pharm. Experim. Therap.*, vol. 315, No. 2, pp. 553-562, 2005.
McDonald et al., "Semicarbazide Sensitive Amine Oxidase and Vascular Adhesion Protein-1: One Protein Being Validated as a Therapeutic Target for Inflammatory Diseases", *Annual Reports in Medicinal Chemistry*, vol. 42, pp. 229-243, 2007.
Noda et al., "Inhibition of Vascular Adhesion Protein-1 Suppresses Endotoxin-Induced Uveitis", *FASEB J.*, vol. 22, pp. 1094-1103, 2008.
Noda et al., "Vascular Adhesion Protein-1 Blockade Suppresses Choroidal Neovascularization", *FASEB J.*, vol. 22, pp. 2928-2935, 2008.

Weston et al., "Hepatic Consequences of Vascular Adhesion Protein-1 Expression", *J. Neural Transm.*, vol. 118, pp. 1055-1064, 2011.
Singh et al., "Expression of Vascular Adhesion Protein-1 in Normal and Inflamed Mice Lungs and Normal Human Lungs", *Virchows Arch.*, vol. 442, pp. 491-495, 2003.
Yoong et al., "Vascular Adhesion Protein-1 and ICAM-1 Support the Adhesion of Tumor-Infiltrating Lymphocytes to Tumor Endothelium in Human Hepatocellular Carcinoma", *J. Immunol.*, vol. 160, pp. 3978-3988, 1998.
Irjala et al., "Vascular Adhesion Protein 1 Mediates Binding of Immunotherapeutic Effector Cells to Tumor Endothelium", *J. Immunol.*, vol. 166, pp. 6937-6943, 2001.
Forster-Horváth et al., "Loss of Vascular Adhesion Protein-1 Expression in Intratumoral Microvessels of Human Skin Melanoma", *Melanoma Research*, vol. 14, pp. 135-140, 2004.
Marttila-Ichihara et al., "Small-Molecule Inhibitors of Vascular Adhesion Protein-1 Reduce the Accumulation of Myeloid Cells into Tumors and Attenuate Tumor Growth in Mice", *J. Immunol.*, vol. 184, pp. 3164-3173, 2010.
Yu, "Amorphous Pharmaceutical Solids: Preparation, Characterization and Stabilization", *Advanced Drug Delivery Reviews*, vol. 48, No. 1, pp. 27-42, 2001.
Caira, "Crystalline Polymorphism of Organic Compounds", *Topics in Current Chemistry*, vol. 198 , pp. 163-208, 1998.
Bastin et al., "Salt Selection and Optimisation Procedures for Pharmaceutical New Chemical Entities", *Organic Process Research & Development*, vol. 4, No. 5, pp. 427-435, 2000.
Lewinsohn, "Mammalian Monoamine-Oxidizing Enzymes, With Special Reference to Benzylamine Oxidase in Human Tissues", *Brazilian J. Med. Biol. Res.*, vol. 17, pp. 223-256, 1984.
Morin et al., "Semicarbazide-Sensitive Amine Oxidase Substrates Stimulate Glucose Transport and Inhibit Lipolysis in Human Adipocytes", *The Journal of Phamacology and Experimental Therapeutics*, vol. 297, pp. 563-572, 2001.
Yu et al., "Characterization of Human Serum and Umbilical Artery Semicarbazide-Sensitive Amino Oxidase (SSAO)", *Biochemical Pharmacology*, vol. 47, No. 6, pp. 1055-1059, 1994.
Salmi et al., "VAP-1: An Adhesin and an Enzyme", *TRENDS in Immunology*, vol. 22, pp. 211-216, 2001.
Yu et al., "Physiological and Pathological Implications of Semicarbazide-Sensitive Amine Oxidase.", *Biochim. Biophys. Acta*, vol. 1647, pp. 193-199, 2003.
Ekblom, "Potential Therapeutic Value of Drugs Inhibiting Semicarbazide-Sensitive Amino Oxidase: Vascular Cytoprotection in *Diabetes Mellitus*", *Pharmacological Research*, vol. 37, No. 2, pp. 87-92, 1998.
Brittain, "Developing an Appropriate Salt Form for an Active Phamaceutical Ingredient", *American Pharmaceutical Review*, 5 pages, 2009.
Bauer, "Pharmaceutical Solids—The Amorphous Phase", *Journal of Validation Technology*, pp. 63-68, 2009.
International Search Report and Written Opinion of the ISA issued in PCT/GB2016/051122, dated Jun. 29, 2016.
Mar. 10, 2009 International-Type Search Report issued in priority application SE 0801979-6.
Arcari et al., "Anti-ulcer and Antisecretory Activity of Selected Imidazopiperidines", *Arzneim.-Forsch./Drug Res.* 34 (11), Nr. II (1984), pp. 1467-1471, including compound 13; the first paragraph of the left column of p. 1468; entry 12 of table 3.
Byrn, Solid State Chemistry of Drugs, 2nd edition. 1999, SSCI Inc, Chapter 10, Polymorphs, pp. 232-247.
Dunkel et al., Semicarbazide-Sensitive Amine Oxidase/Vascular Adhesion Protein-1: A Patent Survey, 2011, *Expert Opin. Ther. Patents*, vol. 21, No. 9, p. 1453-1471, 2011.
International Search Report issued in PCT/EP2009/062011, dated Nov. 2009.
Magyar, Semicarbazide-Sensitive Amine Oxidase—Its Physiological Significance, *Pure Appl. Chem*, vol. 73, No. 9, pp. 1393-1400, 2001.
International Search Report and Written Opinion of the ISA issued in PCT/GB2016/051119, dated Jun. 29, 2016.

(56) References Cited

OTHER PUBLICATIONS

U.S. Appl. No. 15/567,755, which is a National Stage of PCT/GB2016/051122, filed Apr. 22, 2016.
U.S. Appl. No. 15/567,555, which is a National Stage of PCT/GB2016/051122, filed Apr. 22, 2016.

* cited by examiner

PHARMACEUTICAL SALT FORMS OF AN INHIBITOR OF SEMICARBAZIDE-SENSITIVE AMINE OXIDASE (SSAO)

FIELD OF THE INVENTION

The present invention relates to new salt forms of (3S)-Tetrahydrofuran-3-yl (4S)-4-isopropyl-1,4,6,7-tetrahydro-5H-imidazo[4,5-c]pyridine-5-carboxylate, and to their use in medicine.

BACKGROUND OF THE INVENTION

Semicarbazide-sensitive amine oxidase (SSAO) activity is an enzyme activity expressed by Vascular Adhesion Protein-1 (VAP-1) or Amine Oxidase, Copper Containing 3 (AOC3), belongs to the copper-containing amine oxidase family of enzymes (EC.1.4.3.6). Therefore inhibitors of the SSAO enzyme may also modulate the biological functions of the VAP-1 protein.

SSAO activity has been found in a variety of tissues including vascular and non-vascular smooth muscle tissue, endothelium, and adipose tissue [Lewinsohn, *Braz. J. Med. Biol. Res.* 1984, 17, 223-256; Nakos & Gossrau, *Folia Histochem. Cytobiol.* 1994, 32, 3-10; Yu et al., *Biochem. Pharmacol.* 1994, 47, 1055-1059; Castillo et al., *Neurochem. Int* 1998, 33, 415-423; Lyles & Pino, *J. Neural. Transm.* Suppl. 1998, 52, 239-250; Jaakkola et al., *Am. J. Pathol.* 1999, 155, 1953-1965; Morin et al., *J. Pharmacol. Exp. Ther.* 2001, 297, 563-572; Salmi & Jalkanen, *Trends Immunol.* 2001, 22, 211-216]. In addition, SSAO protein is found in blood plasma and this soluble form appears to have similar properties as the tissue-bound form [Yu et al., *Biochem. Pharmacol.* 1994, 47, 1055-1059; Kurkijärvi et al., *J. Immunol.* 1998, 161, 1549-1557].

The precise physiological role of this abundant enzyme has yet to be fully determined, but it appears that SSAO and its reaction products may have several functions in cell signalling and regulation. For example, recent findings suggest that SSAO plays a role in both GLUT4-mediated glucose uptake [Enrique-Tarancon et al., *J. Biol. Chem.* 1998, 273, 8025-8032; Morin et al., *J. Pharmacol. Exp. Ther.* 2001, 297, 563-572] and adipocyte differentiation [Fontana et al., *Biochem. J.* 2001, 356, 769-777; Mercier et al., *Biochem. J.* 2001, 358, 335-342]. In addition, SSAO has been shown to be involved in inflammatory processes where it acts as an adhesion protein for leukocytes [Salmi & Jalkanen, *Trends Immunol.* 2001, 22, 211-216; Salmi & Jalkanen, in "*Adhesion Molecules: Functions and Inhibition*" K. Ley (Ed.), 2007, pp. 237-251], and might also play a role in connective tissue matrix development and maintenance [Langford et al., *Cardiovasc. Toxicol.* 2002, 2(2), 141-150; Göktürk et al., *Am. J. Pathol.* 2003, 163(5), 1921-1928]. Moreover, a link between SSAO and angiogenesis has recently been discovered [Noda et al., *FASEB J.* 2008, 22(8), 2928-2935], and based on this link it is expected that inhibitors of SSAO have an anti-angiogenic effect.

Several studies in humans have demonstrated that SSAO activity in blood plasma is elevated in conditions such as congestive heart failure, diabetes mellitus, Alzheimer's disease, and inflammation [Lewinsohn, *Braz. J. Med. Biol. Res.* 1984, 17, 223-256; Boomsma et al., *Cardiovasc. Res.* 1997, 33, 387-391; Ekblom, *Pharmacol. Res.* 1998, 37, 87-92; Kurkijärvi et al., *J. ImmunoL* 1998, 161, 1549-1557; Boomsma et al., *Diabetologia* 1999, 42, 233-237; Meszaros et al., *Eur. J. Drug Metab. Pharmacokinet.* 1999, 24, 299-302; Yu et al., *Biochim. Biophys. Acta* 2003, 1647(1-2), 193-199; Mátyus et al., *Curr. Med. Chem.* 2004, 11(10), 1285-1298; O'Sullivan et al., *Neurotoxicology* 2004, 25(1-2), 303-315; del Mar Hernandez et al., *Neurosci. Lett.* 2005, 384(1-2), 183-187]. It has been suggested that reactive aldehydes and hydrogen peroxide produced by endogenous amine oxidases contribute to the progression of cardiovascular diseases, diabetic complications and Alzheimer's disease [Callingham et al., *Prog. Brain Res.* 1995, 106, 305-321; Ekblom, *Pharmacol. Res.* 1998, 37, 87-92; Yu et al., *Biochim. Biophys. Acta* 2003, 1647(1-2), 193-199; Jiang et al., *Neuropathol Appl Neurobiol.* 2008, 34(2), 194-204]. Furthermore, the enzymatic activity of SSAO is involved in the leukocyte extravasation process at sites of inflammation where SSAO has been shown to be strongly expressed on the vascular endothelium [Salmi et al., *Immunity* 2001, 14(3), 265-276; Salmi & Jalkanen, in "*Adhesion Molecules: Functions and Inhibition*" K. Ley (Ed.), 2007, pp. 237-251]. Accordingly, inhibition of SSAO has been suggested to have a therapeutic value in the prevention of diabetic complications and in inflammatory diseases [Ekblom, *Pharmacol. Res.* 1998, 37, 87-92; Salmi et al., *Immunity* 2001, 14(3), 265-276; Salter-Cid et al., *J. Pharmacol. Exp. Ther.* 2005, 315(2), 553-562].

WO2007/146188 teaches that blocking SSAO activity inhibits leucocyte recruitment, reduces the inflammatory response, and is expected to be beneficial in prevention and treatment of seizures, for example, in epilepsy.

O'Rourke et al (J Neural Transm. 2007; 114(6):845-9) examined the potential of SSAO inhibitors in neurological diseases, having previously demonstrated the efficacy of SSAO inhibition in a rat model of stroke. An SSAO inhibitor is tested on relapsing-remitting experimental autoimmune encephalomyelitis (EAE), a mouse model that shares many characteristics with human multiple sclerosis. The data demonstrates the potential clinical benefit of small molecule anti-SSAO therapy in this model and therefore in treatment of human multiple sclerosis.

SSAO knockout animals are phenotypically overtly normal but exhibit a marked decrease in the inflammatory responses evoked in response to various inflammatory stimuli [Stolen et al., *Immunity* 2005, 22(1), 105-115]. In addition, antagonism of its function in wild type animals in multiple animal models of human disease (e.g. carrageenan-induced paw inflammation, oxazolone-induced colitis, lipopolysaccharide-induced lung inflammation, collagen-induced arthritis, endotoxin-induced uveitis) by the use of antibodies and/or small molecules has been shown to be protective in decreasing the leukocyte infiltration, reducing the severity of the disease phenotype and reducing levels of inflammatory cytokines and chemokines [Kirton et al., *Eur. J. ImmunoL* 2005, 35(11), 3119-3130; Salter-Cid et al., *J. Pharmacol. Exp. Ther.* 2005, 315(2), 553-562; McDonald et al., *Annual Reports in Medicinal Chemistry* 2007, 42, 229-243; Salmi & Jalkanen, in "*Adhesion Molecules: Functions and Inhibition*" K. Ley (Ed.), 2007, pp. 237-251; Noda et al., *FASEB J.* 2008 22(4), 1094-1103; Noda et al., *FASEB J.* 2008, 22(8), 2928-2935]. This anti-inflammatory protection seems to be afforded across a wide range of inflammatory models all with independent causative mechanisms, rather than being restricted to one particular disease or disease model. This would suggest that SSAO may be a key nodal point for the regulation of the inflammatory response, and it is therefore likely that SSAO inhibitors will be effective anti-inflammatory drugs in a wide range of human diseases. VAP-1 has also been implicated in the progression and maintenance of fibrotic diseases including those of the liver and lung. Weston and Adams (J Neural Transm. 2011, 118(7), 1055-64) have summarised the experimental data implicating VAP-1 in liver fibrosis, and Weston et al (EASL Poster 2010) reported that blockade of VAP-1 accelerated the resolution of carbon tetrachloride induced fibrosis. In addition VAP-1 has been implicated in inflammation of the lung (e.g. Singh et al., 2003, Virchows Arch 442:491-495) suggesting that VAP-1 blockers would reduce lung inflammation and thus be of benefit to the treatment of cystic fibrosis by treating both the pro-fibrotic and pro-inflammatory aspects of the disease.

SSAO (VAP-1) is up regulated in gastric cancer and has been identified in the tumour vasculature of human melanoma, hepatoma and head and neck tumours (Yoong K F, McNab G, Hubscher S G, Adams D H. (1998), J Immunol 160, 3978-88.; lrjala H, Salmi M, Alanen K, Gre'nman R, Jalkanen S (2001), Immunol. 166, 6937-6943; Forster-Horvath C, Dome B, Paku S, et al. (2004), Melanoma Res. 14, 135-40.). One report (Marttila-lchihara F, Castermans K, Auvinen K, Oude Egbrink M G, Jalkanen S, Griffioen A W, Salmi M. (2010), J Immunol. 184, 3164-3173.) has shown that mice bearing enzymically inactive VAP-1 grow melanomas more slowly, and have reduced tumour blood vessel number and diameter. The reduced growth of these tumours was also reflected in the reduced (by 60-70%) infiltration of myeloid suppressor cells. Encouragingly VAP-1 deficiency had no effect on vessel or lymph formation in normal tissue.

For the above reasons, it is expected that inhibition of SSAO will reduce the levels of pro-inflammatory enzyme products (aldehydes, hydrogen peroxide and ammonia) whilst also decreasing the adhesive capacity of immune cells and correspondingly their activation and final extra-vasation. Diseases where such an activity is expected to be therapeutically beneficial include all diseases where immune cells play a prominent role in the initiation, maintenance or resolution of the pathology, such inflammatory diseases and immune/autoimmune diseases. Examples of such diseases include multiple sclerosis, arthritis and vasculitis.

An unmet medical need exists for new and improved inhibitors of SSAO. WO2010/031789 (the content of which is herein incorporated by reference) discloses a promising class of SSAO inhibitor compounds, especially promising is Example 16, which is the free base of (3S)-Tetrahydrofuran-3-yl (4S)-4-isopropyl-1,4,6,7-tetrahydro-5H-imidazo[4,5-c]pyridine-5-carboxylate, and has the following structure:

The free base of (3S)-Tetrahydrofuran-3-yl (4S)-4-isopropyl-1,4,6,7-tetrahydro-5H-imidazo[4,5-c]pyridine-5-carboxylate is an hygroscopic amorphous glass/gum. The glass transition point is at the relatively low temperature of 39° C., so the free base frequently exists as a gum.

The invention described herein relates to new salt forms of the SSAO inhibitor (3S)-Tetrahydrofuran-3-yl (4S)-4-isopropyl-1,4,6,7-tetrahydro-5H-imidazo[4,5-c]pyridine-5-carboxylate having surprisingly improved properties.

SUMMARY OF THE INVENTION

Hygroscopicity is an undesirable property for a pharmaceutical drug because the incorporation of water results in a number of problems. Examples of such problems include difficulty weighing the drug due to the variable mass of water, and difficulty handling the drug due to its tendency to become sticky. Gums are generally undesirable because they are sticky and difficult to handle. Crystals are preferable over amorphous gums because they have better filtration properties, and are therefore easier to dry.

Good thermal stability is a desirable property for a pharmaceutical drug. It is well known that temperatures routinely exceed 50° C. during standard milling and tablet pressing procedures (see e.g. Developing Solid Oral Dosage Forms: Pharmaceutical Theory & Practice; Yihong Qiu, Yisheng Chen, Geoff G. Z. Zhang, Lirong Liu, William Porter, 2009). There is a significant risk that a 'hot spot' will occur during the milling or tableting process, and that the temperature of that hot spot will exceed the melting point of the drug. The presence of molten drug in the milling or pressing process is expected to cause drug particles to clump together, or otherwise form aggregates. Such melting, clumping or aggregation is expected to hamper accuracy and consistency.

Following extensive investigation into the preparation and properties of (3S)-Tetrahydrofuran-3-yl (4S)-4-isopropyl-1,4,6,7-tetrahydro-5H-imidazo[4,5-c]pyridine-5-carboxylate free base and salt forms thereof, the applicants have discovered advantageous salt forms, namely the mesylate salt which has advantageously high thermal stability, and advantageously low hygroscopicity; and the sulphate salt, which exists as a hydrate, having advantageously high thermal stability, and advantageously low hygroscopicity.

The present invention includes a composition comprising the sulphate or mesylate salts of (3S)-Tetrahydrofuran-3-yl (4S)-4-isopropyl-1,4,6,7-tetrahydro-5H-imidazo[4,5-c]pyridine-5-carboxylate, and one or more pharmaceutically acceptable excipients.

The sulphate and mesylate salts of (3S)-Tetrahydrofuran-3-yl (4S)-4-isopropyl-1,4,6,7-tetrahydro-5H-imidazo[4,5-c]pyridine-5-carboxylate are expected to be useful in the treatment of inflammation, an inflammatory disease, an immune or an autoimmune disorder, or inhibition of tumour growth. In an embodiment the the inflammation or inflammatory disease or immune or autoimmune disorder is arthritis (including rheumatoid arthritis, juvenile rheumatoid arthritis, osteoarthritis and psoriatic arthritis), synovitis, vasculitis, Sjogren's disease, a condition associated with inflammation of the bowel (including Crohn's disease, ulcerative colitis, inflammatory bowel disease and irritable bowel syndrome), atherosclerosis, multiple sclerosis, Alzheimer's disease, vascular dementia, Parkinson's disease, cerebral amyloid angiopathy, cerebral autosomal dominant arteriopathy with subcortical infarcts and leukoencephalopathy, a pulmonary inflammatory disease (including asthma, chronic obstructive pulmonary disease and acute respiratory distress syndrome), a fibrotic disease (including idiopathic pulmonary fibrosis, cardiac fibrosis, liver fibrosis and systemic sclerosis (scleroderma)), an inflammatory disease of the skin (including contact dermatitis, atopic dermatitis and psoriasis), an inflammatory disease of the eye (including age related macular degeneration, uveitis and diabetic retinopathy), systemic inflammatory response syndrome, sepsis, an inflammatory and/or autoimmune condition of the liver (including autoimmune hepatitis, primary biliary cirrhosis, alcoholic liver disease, sclerosing cholangitis, and autoimmune cholangitis), diabetes (type I or II) and/or the complications thereof, chronic heart failure, congestive heart failure, an ischemic disease (including stroke and ischemia-reperfusion injury) or myocardial infarction and/or the complications thereof, or epilepsy.

The present invention includes the use of said sulphate and mesylate salts of (3S)-Tetrahydrofuran-3-yl (4S)-4-isopropyl-1,4,6,7-tetrahydro-5H-imidazo[4,5-c]-pyridine-5-carboxylate in the manufacture of a medicament for the treatment or prevention of the above-mentioned conditions and diseases. The invention also includes methods for treatment or prevention of such conditions and diseases, comprising administering to a mammal, including man, in need of such treatment an effective amount of a compound as defined above.

DETAILED DESCRIPTION OF THE INVENTION

Figure 1:
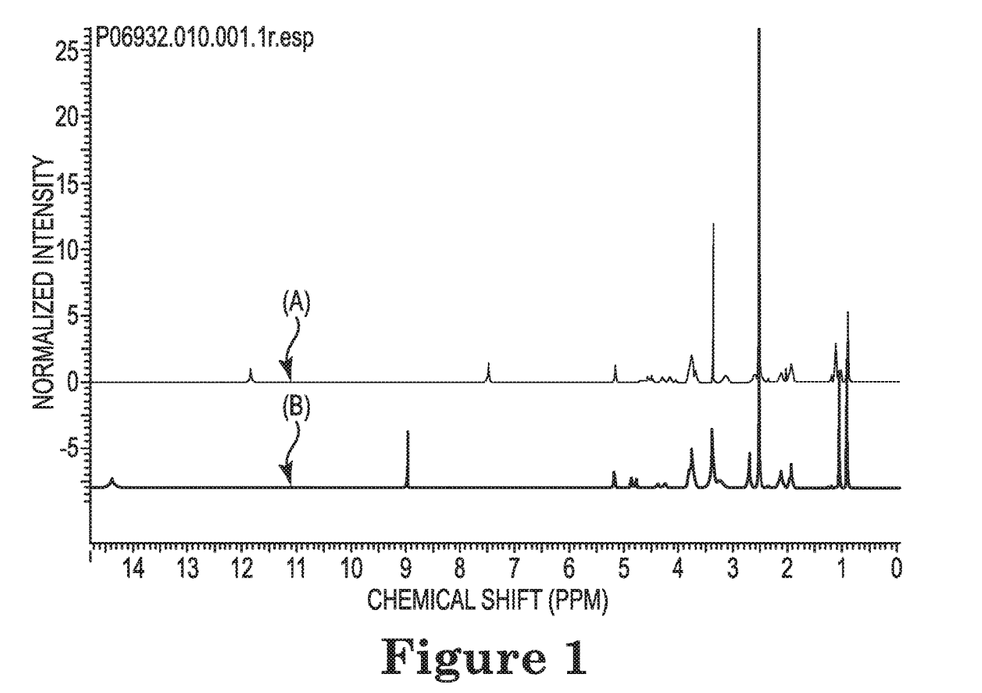
FIG. 1 shows the 1H NMR spectra of (3S)-Tetrahydrofuran-3-yl (4S)-4-isopropyl-1,4,6,7-tetrahydro-5H-imidazo[4,5-c]pyridine-5-carboxylate free base (labelled (A)) and the hydrochloride salt (labelled (B)).
Figure 2:
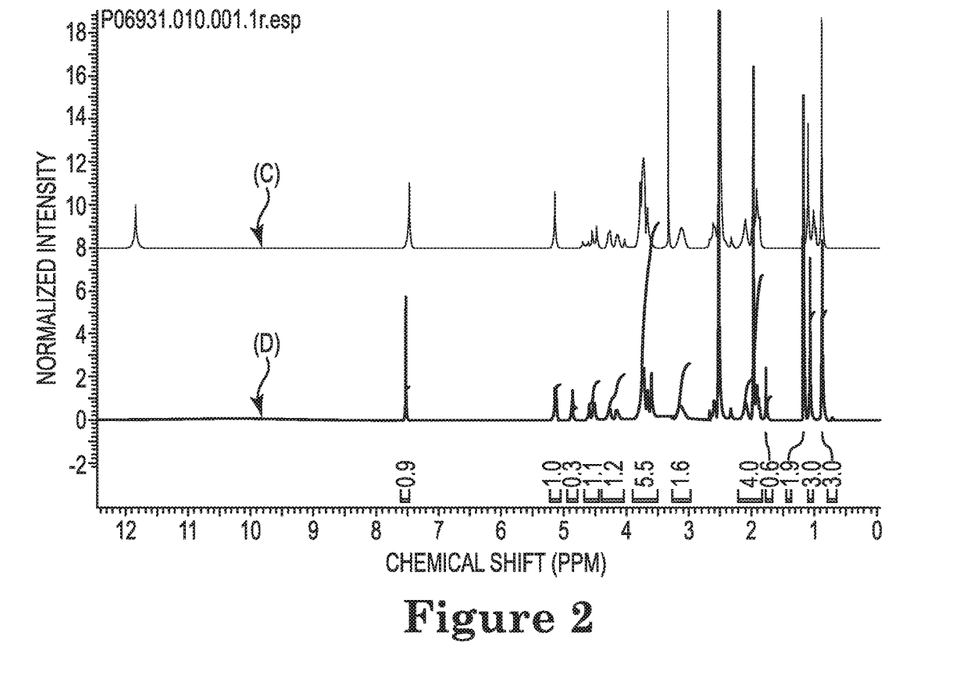
FIG. 2 shows the 1H NMR spectra of (3S)-Tetrahydrofuran-3-yl (4S)-4-isopropyl-1,4,6,7-tetrahydro-5H-imidazo[4,5-c]pyridine-5-carboxylate free base (labelled (C)) and the phosphate salt (labelled (D)).

Following lengthy research into the formation of salts by reaction of (3S)-Tetrahydrofuran-3-yl (4S)-4-isopropyl-1,4,6,7-tetrahydro-5H-imidazo[4,5-c]pyridine-5-carboxylate with 22 acids (hydrochloric acid, sulphuric acid, 1,2-ethanedisulphonic acid, p-toluenesulphonic acid, methanesulphonic acid, benzenesulphonic acid, L-aspartic acid, maleic acid, phosphoric acid, ethanesulphonic acid, L-glutamic acid, L-tartaric acid, fumaric acid, citric acid, L-malic acid, D-gluconic acid, D/L-lactic acid, L-lactic acid, Benzoic acid, Succinic acid, adipic acid, and acetic acid), the applicant discovered four novel crystalline salt forms, namely:

(3S)-Tetrahydrofuran-3-yl (4S)-4-isopropyl-1,4,6,7-tetrahydro-5H-imidazo[4,5-c]-pyridine-5-carboxylate hydrochloride;

(3S)-Tetrahydrofuran-3-yl (4S)-4-isopropyl-1,4,6,7-tetrahydro-5H-imidazo[4,5-c]-pyridine-5-carboxylate phosphate;

(3S)-Tetrahydrofuran-3-yl (4S)-4-isopropyl-1,4,6,7-tetrahydro-5H-imidazo[4,5-c]-pyridine-5-carboxylate sulphate hydrate; and (3S)-Tetrahydrofuran-3-yl (4S)-4-isopropyl-1,4,6,7-tetrahydro-5H-imidazo[4,5-c]-pyridine-5-carboxylate mesylate.

The salts formed by reaction of the free base with 1,2-ethanedisulphonic acid, p-toluenesulphonic acid, benzenesulphonic acid, L-aspartic acid, maleic acid, ethanesulphonic acid, L-glutamic acid, L-tartaric acid, fumaric acid, citric acid, L-malic acid, D-gluconic acid, D/L-lactic acid, L-lactic acid, benzoic acid, buccinic acid, adipic acid, and acetic acid were found to be non-crystalline.

The four crystalline salts were tested in order to determine their ease of handling, hygroscopicity, and thermal stability. The hydrochloride and phosphate salts have the advantage of improved handling properties over the free base glass/gum by virtue of their crystallinity. However, preliminary studies indicate that both salts forms are somewhat hygroscopic. Both salts deliquesced on overnight storage at 40° C. in an environment having 75% relative humidity.

The mesylate and sulphate salts have the advantage of improved handling properties over the free base gum by virtue of their crystallinity. Both salts have surprisingly reduced hygroscopicity. The mesylate salt deliquesced following storage for 3 days at 40° C. in an environment having 75% relative humidity. The sulphate salt was unchanged after storage for 7 days at 40° C. in an environment having 75% relative humidity.

The mesylate and sulphate salts have the advantage of significantly improved thermal stability. The mesylate has a melting point of 189° C. The sulphate has a melting point of 106° C. Based on these melting points, both the mesylate and sulphate salts are expected to survive the milling and pressing procedures without melting or otherwise hampering the process. Thus both the sulphate and mesylate salts have surprisingly improved hygroscopicity and surprisingly improved thermal stability compared to the corresponding free base.

Definitions

"Treatment" as used herein includes prophylaxis of the named disorder or condition, or amelioration or elimination of the disorder once it has been established.

"An effective amount" refers to an amount of a compound that confers a therapeutic effect on the treated subject. The therapeutic effect may be objective (i.e., measurable by some test or marker) or subjective (i.e., subject gives an indication of or feels an effect).

"Pharmaceutically acceptable" means being useful in preparing a pharmaceutical composition that is generally safe, non-toxic and neither biologically nor otherwise undesirable and includes being useful for veterinary use as well as human pharmaceutical use.

Unless stated to the contrary, the term "(3S)-Tetrahydrofuran-3-yl (4S)-4-isopropyl-1,4,6,7-tetrahydro-5H-imidazo[4,5-c]pyridine-5-carboxylate" as used in connection with the salts forms described herein includes a mixture of the (3S,4S) and (3R,4R) enantiomers. In an embodiment (3S)-Tetrahydrofuran-3-yl (4S)-4-isopropyl-1,4,6,7-tetrahydro-5H-imidazo[4,5-c]pyridine-5-carboxylate, and salts thereof, has an absolute purity of >95%, preferably >99%, more preferably >99.5%. In an embodiment (3S)-Tetrahydrofuran-3-yl (4S)-4-isopropyl-1,4,6,7-tetrahydro-5H-imidazo[4,5-c]pyridine-5-carboxylate means the (3S,4S) enantiomer having an enantiomeric purity of >95%, preferably >99%, more preferably >99.5%. In an embodiment (3S)-Tetrahydrofuran-3-yl (4S)-4-isopropyl-1,4,6,7-tetrahydro-5H-imidazo[4,5-c]pyridine-5-carboxylate has a diastereoisomeric purity of >95%, preferably >99%, more preferably >99.5%.

Compositions

For clinical use, the compounds of the invention are formulated into pharmaceutical formulations for various modes of administration. It will be appreciated that compounds of the invention may be administered together with a physiologically acceptable carrier, excipient, or diluent. The pharmaceutical compositions of the invention may be administered by any suitable route, preferably by oral, rectal, nasal, topical (including buccal and sublingual), sublingual, transdermal, intrathecal, transmucosal or parenteral (including subcutaneous, intramuscular, intravenous and intradermal) administration.

Other formulations may conveniently be presented in unit dosage form, e.g., tablets and sustained release capsules, and in liposomes, and may be prepared by any methods well known in the art of pharmacy. Pharmaceutical formulations are usually prepared by mixing the active substance, or a pharmaceutically acceptable salt thereof, with conventional pharmaceutically acceptable carriers, diluents or excipients. Examples of excipients are water, gelatin, gum *arabicum*, lactose, microcrystalline cellulose, starch, sodium starch glycolate, calcium hydrogen phosphate, magnesium stearate, talcum, colloidal silicon dioxide, and the like. Such formulations may also contain other pharmacologically active agents, and conventional additives, such as stabilizers, wetting agents, emulsifiers, flavouring agents, buffers, and the like. Usually, the amount of active compounds is between 0.1-95% by weight of the preparation, preferably between 0.2-20% by weight in preparations for parenteral use and more preferably between 1-50% by weight in preparations for oral administration.

The formulations can be further prepared by known methods such as granulation, compression, microencapsulation, spray coating, etc. The formulations may be prepared by conventional methods in the dosage form of tablets, capsules, granules, powders, syrups, suspensions, suppositories or injections. Liquid formulations may be prepared by dissolving or suspending the active substance in water or other suitable vehicles. Tablets and granules may be coated in a conventional manner. To maintain therapeutically effective plasma concentrations for extended periods of time, compounds of the invention may be incorporated into slow release formulations.

The dose level and frequency of dosage of the specific compound will vary depending on a variety of factors including the potency of the specific compound employed, the metabolic stability and length of action of that compound, the patient's age, body weight, general health, sex, diet, mode and time of administration, rate of excretion, drug combination, the severity of the condition to be treated, and the patient undergoing therapy. The daily dosage may, for example, range from about 0.001 mg to about 100 mg per kilo of body weight, administered singly or multiply in doses, e.g. from about 0.01 mg to about 25 mg each. Normally, such a dosage is given orally but parenteral administration may also be chosen.

Experimental Methods
Salt Formation Experiments

A salt screen was carried out using 24 acidic counter-ions (see Table 1), in an attempt to form both mono and hemi salts, where appropriate. Nine sets of experiments were performed using a diverse range of solvent systems and conditions Slow Cooling Salt Formation Experiments Separate samples of (3S)-Tetrahydrofuran-3-yl (4S)-4-isopropyl-1,4,6,7-tetrahydro-5H-imidazo[4,5-c]pyridine-5-carboxylate free base (20 mg) were dissolved in IPA (2.5 vol), IPAc (2.5 vol), acetone-water (9:1 v/v, 2.5 vol) or DIPE (10 vol). The solutions were heated to 40° C. and each test acid (1 or 0.5 equivalents, see Table 1) was added with gentle stirring. The vials were held at 40° C. for 1 h and were then allowed to cool to 5° C., at 1° C./min. The mixtures were kept at 5° C. overnight. All solids obtained were collected by filtration and analysed by XRPD. Oils and gums were subjected to maturation cycles, RT to 50° C., 4 h at each temperature, to favour crystallisation. Solutions were allowed to evaporate at ambient conditions. The residues were analysed by $^1$H-NMR and DSC to assess salt formation and/or potential crystallisation upon heating.

Anti-Solvent Addition Salt Formation Experiments

Separate samples of (3S)-Tetrahydrofuran-3-yl (4S)-4-isopropyl-1,4,6,7-tetrahydro-5H-imidazo[4,5-c]pyridine-5-carboxylate free base (15 mg) were dissolved in IPAc (with and without 3% v/v of water; 5 vol), and the solutions were heated to 40° C. The corresponding acids (1 or 0.5 equivalents, see Table 1) were added with gentle stirring. The vials were held at 40° C. for 1 h, then increasing amounts of anti-solvent (n-heptane or TBME) were added, until the solutions became cloudy. At this point, all the samples were cooled to 5° C., at 1° C./minute, and held at 5° C. overnight. More anti-solvent was added where no precipitation had occurred. All solids obtained were collected by filtration and analysed by XRPD. Oils and gums were subjected to maturation cycles, RT to 50° C., 4 h at each temperature, to favour crystallisation. Solutions were cooled down to sub-ambient temperature and allowed to evaporate if no precipitation occurred.

Analytical Methods
X-Ray Powder Diffraction (XRPD)

X-Ray Powder Diffraction patterns were collected on a Bruker AXS C2 GADDS diffractometer using Cu Kα radiation (40 kV, 40 mA), automated XYZ stage, laser video microscope for auto-sample positioning and a HiStar 2-dimensional area detector. X-ray optics consisted of a single Göbel multilayer mirror coupled with a pinhole collimator of 0.3 mm. A weekly performance check is carried out using a certified standard NIST 1976 Corundum (flat plate). The beam divergence, i.e. the effective size of the X-ray beam on the sample, was approximately 4 mm. A θ-θ continuous scan mode was employed with a sample to detector distance of 20 cm which gives an effective 2θ range of 3.2°-29.7°. Typically the sample would be exposed to the X-ray beam for 120 seconds. The software used for data collection was GADDS for WNT 4.1.16 and the data were analysed and presented using Diffrac Plus EVA v 9.0.0.2 or v 13.0.0.2. Samples run under ambient conditions were prepared as flat plate specimens using powder as received without grinding. Approximately 1-2 mg of the sample was lightly pressed on a glass slide to obtain a flat surface. Samples run under non-ambient conditions were mounted on a silicon wafer with heat conducting compound. The sample was then

TABLE 1

Acids used for salt formation experiments

| Counter ion | Added as | Counter ion | Added as |
|---|---|---|---|
| Hydrochloric acid | 1M in THF | L-tartaric acid | 1M in THF |
| Sulphuric acid | 1M in THF | Fumaric acid | 0.5M in THF:MeOH |
| 1,2-Ethanedisulphonic acid | 1M in THF | Citric acid | 1M in THF |
| p-toluenesulphonic acid | 1M in EtOH | L-Malic acid | 1M in THF |
| Methane sulphonic acid | 1M in THF | D-Gluconic acid | 50% w/w water |
| Benzene sulphonic acid | 1M in THF | D/L-Lactic acid | liquid |
| L-Aspartic acid | solid | L-Lactic acid | 1M in THF |
| Maleic acid | 1M in THF | Benzoic acid | 1M in IPA |
| Phosphoric acid | 1M in THF | Succinic acid | 1M in MeOH |
| Ethane sulphonic acid | 1M in THF | Adipic acid | 1M in MeOH:THF |
| L-Glutamic acid | solid | acetic acid | 1M in THF | heated to the appropriate temperature at ca 10° C./min and subsequently held isothermally for ca 1 min before data collection was initiated.

Alternatively, X-Ray Powder Diffraction patterns were collected on a Bruker D8 diffractometer using Cu Kα radiation (40 kV, 40 mA), θ-2θ goniometer, and divergence of V4 and receiving slits, a Ge monochromator and a Lynxeye detector. The instrument is performance checked using a certified Corundum standard (NIST 1976). The software used for data collection was Diffrac Plus XRD Commander v2.5.0 and the data were analysed and presented using Diffrac Plus EVA v 11.0.0.2 or v 13.0.0.2. Samples were run under ambient conditions as flat plate specimens using powder as received. Approximately 20 mg of the sample was gently packed into a cavity cut into polished, zerobackground (510) silicon wafer. The sample was rotated in its own plane during analysis. The details of the data collection are—angular range: 2 to 42° 2θ; step size: 0.05° 2θ; collection time: 0.5 s/step.

Nuclear Magnetic Resonance (NMR)

$^1$H NMR spectra were collected on a Bruker 400 MHz instrument equipped with an auto sampler and controlled by a DRX400 console. Automated experiments were acquired using ICONNMR v4.0.4 (build 1) running with Topspin v 1.3 (patch level 10) using the standard Bruker loaded experiments. For non-routine spectroscopy, data were acquired through the use of Topspin alone. Samples were prepared in d6-DMSO, unless otherwise stated. Off-line analysis was carried out using ACD SpecManager v 12.00 (build 29094). Alternatively, $^1$H NMR spectra were collected on a Bruker Avance III 400 MHz QNP Ultrashield Plus Cryo.

Liquid Chromatography-Mass Spectrometry (LCMS)

Analytical LCMS was performed on an Agilent 1100 HPLC system with a Waters ZQ mass spectrometer using a Phenomenex Synergi column (RP-Hydro, 150×4.6 mm, 4 um, 1.5 mL/min, 30° C., gradient 5-100% MeCN (+0.085% TFA) in water (+0.1% TFA) over 7 min-held for 0.5 min, 200-300 nm).

Differential Scanning calorimetry (DSC)

DSC data were collected on a TA Instruments Q2000 equipped with a 50 position autosampler. The calibration for thermal capacity was carried out using sapphire and the calibration for energy and temperature was carried out using certified indium. Typically 0.5-3 mg of each sample, in a pin-holed aluminium pan, was heated at 10° C./min from 25° C. to 350° C. A purge of dry nitrogen at 50 mL/min was maintained over the sample. Modulated temperature DSC was carried out using an underlying heating rate of 2° C./min and temperature modulation parameters of ±1.27° C./min and 60 seconds. The instrument control software was Advantage for Q Series v2.8.0.392 and Thermal Advantage v4.8.3 and the data were analysed using Universal Analysis v4.3A.

Thermo-Gravimetric Analysis (TGA)

TGA data were collected on a TA Instruments Q500 TGA, equipped with a 16 position autosampler. The instrument was temperature calibrated using certified Alumel and Nickel. Typically 5-30 mg of each sample was loaded onto a pre-tared platinum crucible and aluminium DSC pan, and was heated at 10° C./min from ambient temperature to 350° C. A nitrogen purge at 60 mL/min was maintained over the sample. The instrument control software was Advantage for Q Series v2.8.0.392 and Thermal Advantage v4.8.3

Polarised Light Microscopy (PLM)

Samples were studied on a Leica LM/DM polarised light microscope with a digital video camera for image capture. A small amount of each sample was placed on a glass slide, mounted in immersion oil and covered with a glass slip, the individual particles being separated as well as possible. The sample was viewed with appropriate magnification and partially polarised light, coupled to a lambda false-colour filter.

Hot Stage Microscopy (HSM) [Melting Point]

Hot Stage Microscopy was carried out using a Leica LM/DM polarised light microscope combined with a Mettler-Toledo MTFP82HT hot-stage and a digital video camera for image capture. A small amount of each sample was placed onto a glass slide with individual particles separated as well as possible. The sample was viewed with appropriate magnification and partially polarised light, coupled to a lambda false-colour filter, whilst being heated from ambient temperature typically at 10-20° C./min.

Chemical Purity Determination by HPLC

Purity analysis was performed on an Agilent HP1100 series system equipped with a diode array detector and using ChemStation software vB.02.01-SR1 using the method detailed below.

| Sample Preparation | 0.5 mg/ml in acetonitrile:water 1:1 |
|---|---|
| Column | Supelco Ascentis Express C18, 100 × 4.6 mm, 2.7 μm |
| Column Temperature (° C.) | 25 |
| Injection (μl) | 5 |
| Wavelength, Bandwidth (nm) | 255, 90 nm |
| Flow Rate (ml · min$^{-1}$) | 2.0 |
| Phase A | 0.1% TFA in water |
| Phase B | 0.085% TFA in acetonitrile |

| | Time (min) | % Phase A | % Phase B |
|---|---|---|---|
| Timetable: | 0 | 95 | 5 |
| | 6 | 5 | 95 |
| | 6.2 | 95 | 5 |
| | 8 | 95 | 5 |

Chiral Purity Determination by Chiral HPLC

Chiral HPLC was performed on an Agilent 1200 system using an Astec Chirobiotic T 100×4.6 mm 5 um column, polar reverse phase, 150×4.6 mm, 5 um, isocratic 85% MeOH 15% 20 mM ammonium acetate over 10 min, 1.0 mL/min, 220 nm.

Water Determination by Karl Fischer Titration (KF)

The water content of each sample was measured on a Mettler Toledo DL39 Coulometer using Hydranal Coulomat AG reagent and an argon purge. Weighed solid samples were introduced into the vessel on a platinum TGA pan which was connected to a subaseal to avoid water ingress. Approx 10 mg of sample was used per titration and duplicate determinations were made.

Gravimetric Vapour Sorption (GVS)

Sorption isotherms were obtained using a SMS DVS Intrinsic moisture sorption analyser, controlled by DVS Intrinsic Control software v1.0.0.30. The sample temperature was maintained at 25° C. by the instrument controls. The humidity was controlled by mixing streams of dry and wet nitrogen, with a total flow rate of 200 mL/min The relative humidity was measured by a calibrated Rotronic probe (dynamic range of 1.0-100% RH), located near the sample. The weight change, (mass relaxation) of the sample as a function of % RH was constantly monitored by the microbalance (accuracy ±0.005 mg). Typically 5-20 mg of sample was placed in a tared mesh stainless steel basket under ambient conditions. The sample was loaded and unloaded at 40% RH and 25° C. (typical room conditions).

A moisture sorption isotherm was performed as outlined below (2 scans giving 1 complete cycle). The standard isotherm was performed at 25° C. at 10% RH intervals over a 0.5-90% RH range. Data analysis was undertaken in Microsoft Excel using DVS Analysis Suite v6.0.0.7. Method parameters for SMS DVS intrinsic experiments: adsorption scan 1 40-90; desorption/adsorption scan 2 90-0, 0-40; intervals (% RH) 10; number of scans 4; flow rate (mL/min) 200; temperature (° C.) 25; stability (° C./min) 0.2; sorption time (h) 6 h time out. The sample was recovered after completion of the isotherm and re-analysed by XRPD.

Ion Chromatography (IC)

Data were collected on a Metrohm 761 Compact IC (for cations) and a Metrohm 861 Advanced Compact IC (for anions) using IC Net software v2.3. Accurately weighed samples were prepared as stock solutions in an appropriate dissolving solution and diluted 1:9 prior to testing. Quantification was achieved by comparison with standard solutions of known concentration of the ion being analysed. IC Method Parameters for Anion Chromatography: type of method—anion exchange; column—Metrosep A Supp 5-250 (4.0×250 mm); column temperature (° C.) ambient; injection (μl) 20; detection—conductivity detector; flow rate (mL/min) 0.7; eluent 3.2 mM sodium carbonate, 1.0 mM sodium hydrogen carbonate in 5% aqueous acetone.

Results

Crystalline hydrochloride, sulphate, phosphate and mesylate salts were isolated and these were characterised using some or all of XRPD, $^1$H NMR, DSC, TGA, GVS, IC, PLM, HSM, HPLC and KF (see Table 2). The hydrochloride and phosphate salts were highly hygroscopic. The mesylate and sulfate salts were further analysed.

Synthesis of (3S)-Tetrahydrofuran-3-yl (4S)-4-isopropyl-1,4,6,7-tetrahydro-5H-imidazo[4,5-c]pyridine-5-carboxylate, and mesylate and sulphate forms thereof The following abbreviations have been used:
Aq Aqueous
DCM Dichloromethane
DIPEA Diisopropylethylamine
ee Enantiomeric excess
ES$^+$ Electrospray
EtOAc Ethyl acetate
h Hour(s)
HPLC High performance liquid chromatography
HRMS High resolution mass spectrometry
LCMS Liquid chromatography mass spectrometry
M Molar
MeOH Methanol
[MH$^+$] Protonated molecular ion
min Minutes
RP Reverse phase
MS Mass spectrometry
R$_T$ Retention time
sat Saturated
THF Tetrahydrofuran
TFA Trifluoroacetic acid Experimental Methods All reagents were commercial grade and were used as received without further purification, unless otherwise specified. Reagent grade solvents were used in all cases.

Analytical LCMS was performed on a Waters ZQ mass spectrometer connected to an Agilent 1100 HPLC system. Analytical HPLC was performed on an Agilent 1100 system. High-resolution mass spectra (HRMS) were obtained on an Agilent MSD-TOF connected to an Agilent 1100 HPLC system. During the analyses the calibration was checked by two masses and automatically corrected when needed. Spectra are acquired in positive electrospray mode. The acquired mass range was m/z 100-1100. Profile detection of the mass peaks was used. Flash chromatography was performed on either a CombiFlash Companion system equipped with RediSep silica columns or a Flash Master Personal system equipped with Strata SI-1 silica gigatubes. Reverse Phase HPLC was performed on a Gilson system (Gilson 322 pump with Gilson 321 equilibration pump and Gilson 215 autosampler) equipped with Phenomenex Synergi Hydro RP 150×10 mm, YMC ODS-A 100/150×20 mm or Chirobiotic T 250×10 mm columns. Reverse phase column chromatography was performed on a Gilson system (Gilson 321 pump and Gilson FC204 fraction collector) equipped with Merck LiChroprep® RP-18 (40-63 μm) silica columns. The compounds were automatically named using ACD 6.0. All compounds were dried in a vacuum oven overnight.

Analytical HPLC and LCMS data were obtained with:

System A: Phenomenex Synergi Hydro RP (C18, 30×4.6 mm, 4 μm), gradient 5-100% CH$_3$CN (+0.085% TFA) in water (+0.1% TFA), 1.5 mL/min, with a gradient time of 1.75 min, 200 nm, 30° C.; or

System B: Phenomenex Synergi Hydro RP (C18, 150×4.6 mm, 4 μm), gradient 5-100% CH$_3$CN (+0.085% TFA) in water (+0.1% TFA), 1.5 mL/min with a gradient time of 7 min, 200 nm, 30° C.

Chiral HPLC data were obtained with:

System C: Chirobiotic V polar ionic mode (150×4.6 mm), 70% MeOH in 10 mM aq ammonium formate buffer, 1.0 mL/min, over 10 min, 200 nm, 30° C.

Intermediate 1

4-Isopropyl-4,5,6,7-tetrahydro-1H-imidazo[4,5-c] pyridine hydrochloride

Histamine dihydrochloride (61.9 g, 336 mmol) was dissolved in a solution of NaOH (33.6 g, 841 mmol) in water (125 mL) and MeOH (500 mL), and isobutyraldehyde (61.4 mL, 672 mmol) was added. The reaction mixture was heated under reflux at 80° C. for 24 h, cooled to room temperature, the pH was adjusted to 7 with 1 M aq HCl solution (250 mL) and the solvents were removed in vacuo. The residue was dissolved in warm MeOH (300 mL), allowed to stand for 1 h, filtered and the solvents were removed in vacuo. The residue was stirred in MeOH (50 mL) and acetone (400 mL) for 2 h and was cooled to 4° C. for 2 h. The resulting precipitate was filtered and washed with acetone (100 mL) to give 4-isopropyl-4,5,6,7-tetrahydro-1H-imidazo[4,5-c] pyridine hydrochloride (33.0 g, 48.7%) as a white solid.

Analytical LCMS: purity >90% (System A, R$_T$=0.51 min), ES$^+$: 166.4 [MH]$^+$.

Intermediate 2

4-Nitrophenyl 4-isopropyl-1,4,6,7-tetrahydro-5H-imidazo[4,5-c]pyridine-5-carboxylate Intermediate 1 (2.78 g, 8.28 mmol, 60% pure) and DIPEA (5.27 mL, 30.3 mmol) were dissolved in DCM (100 mL). The reaction mixture was cooled to 0° C. and 4-nitrophenyl chloroformate (4.07 g, 20.2 mmol) was added. The reaction mixture was stirred at room temperature for 18 h. The reaction mixture was washed with sat aq NaHCO$_3$ solution (5×100 mL), dried (MgSO$_4$) and the solvents were removed in vacuo to give 4-nitrophenyl 4-isopropyl-1,4,6,7-tetrahydro-5H-imidazo[4,5-c]pyridine-5-carboxylate (5.28 g, crude) as a yellow gum.

Analytical HPLC: purity 41% (System B, R$_T$=4.70 min); Analytical LCMS: purity 86% (System A, R$_T$=1.70 min), ES$^+$: 331.0 [MH]$^+$.

(3S)-Tetrahydrofuran-3-yl (4S)-4-isopropyl-1,4,6,7-tetrahydro-5H-imidazo[4,5-c]pyridine-5-carboxylate NaH (0.40 g, 10.0 mmol, 60% dispersion in mineral oil) was suspended in anhydrous THF (20 mL), cooled to 0° C. and (S)-3-hydroxytetrahydrofuran (0.88 g, 0.68 mL, 10.0 mmol) was added. The suspension was stirred at 0° C. for 30 min then added to a solution of Intermediate 2 (3.30 g, 10.0 mmol, 70% pure) in THF (60 mL) and the reaction mixture was stirred at room temperature. Two additional such portions of NaH and (S)-3-hydroxytetrahydrofuran in THF were added after 5 and 29 h, respectively. After 2 d the reaction mixture was quenched with water (10 mL) and the solvents were removed in vacuo. The residue was dissolved in EtOAc (100 mL), washed with 1 M aq Na$_2$CO$_3$ solution (4×100 mL), dried (MgSO$_4$) and the solvents were removed in vacuo. The residue was purified by column chromatography (normal phase, 20 g, Strata SI-1, silica gigatube, DCM (200 mL) followed by 2%, 4% and 5% MeOH in DCM (200 mL each)) and reverse phase HPLC (YMC ODS-A 100×20 mm, 5 µm, 25 mL/min, gradient 30% to 60% (over 7 min) then 100% (3 min) MeOH in 10% MeOH/water) to give (3S)-tetrahydrofuran-3-yl 4-isopropyl-1,4,6,7-tetrahydro-5H-imidazo[4,5-c]pyridine-5-carboxylate (34.8 mg, 1.1%) as a white solid.

Analytical HPLC: purity 100% (System B, R$_T$=3.63 min); Analytical LCMS: purity 100% (System B, R$_T$=4.01 min), ES$^+$: 280.1 [MH]$^+$.

(3S)-Tetrahydrofuran-3-yl-4-isopropyl-1,4,6,7-tetrahydro-5H-imidazo[4,5-c]pyridine-5-carboxylate (39.91 mg) was dissolved in 10 mM ammonium formate buffer and MeOH (2 mL, 1:1) and purified twice by reverse phase chiral HPLC (Chirobiotic T 250×10 mm, 3 mL/min, isocratic run 70% MeOH in 10 mM ammonium formate buffer (40 min), pH 7.4) to give a single diastereoisomer, (3S)-tetrahydrofuran-3-yl (4S)-4-isopropyl-1,4,6,7-tetrahydro-5H-imidazo[4,5-c]pyridine-5-carboxylate (6.90 mg, 99% ee).

Analytical HPLC: purity 100% (System B, R$_T$=3.63 min); Chiral HPLC: purity 99.5% (System C, R$_T$=2.22 min); Analytical LCMS: purity 100% (System B, R$_T$=3.90 min), ES$^+$: 280.1 [MH]$^+$; HRMS calculated for C$_{14}$H$_{21}$N$_3$O$_3$: 279.1583, found 279.1571.

(3S)-Tetrahydrofuran-3-yl (4S)-4-isopropyl-1,4,6,7-tetrahydro-5H-imidazo[4,5-c]pyridine-5-carboxylate Mesylate (3S)-Tetrahydrofuran-3-yl (4S)-4-isopropyl-1,4,6,7-tetrahydro-5H-imidazo[4,5-c]-pyridine-5-carboxylate free base (460 mg, 1.65 mmol) was dissolved in EtOAc (10 mL) at room temperature to give a clear colourless solution. Methanesulphonic acid (107 uL) was added portion-wise with gentle heating. The solution was allowed to cool to room temperature overnight. The resulting crystals were collected by filtration, washed with EtOAc (2×10 mL) and dried overnight at 40° C. in vacuo. (3S)-Tetrahydrofuran-3-yl (4S)-4-isopropyl-1,4,6,7-tetrahydro-5H-imidazo[4,5-c]pyridine-5-carboxylate mesylate salt was obtained with a 99% yield (615 mg) as a white solid. HPLC: Retention time 2.27 min, purity 99.5%. Melting point: 189° C. LCMS: Retention time 4.19 min, ES$^+$280.0 [MH]$^+$, 100% purity. Chiral HPLC: Retention time 3.70 min, >99.5% de. $^1$H NMR (400 MHz, CDCl$_3$): δ$_H$ 8.72 (1H, m, NHC$\underline{H}$NH$^+$), 5.29 (1H, m, OC$\underline{H}$), 5.05 (0.5H, d, J 8.4 Hz, CC$\underline{H}$N), 4.89 (0.5H, d, J 7.6 Hz, CC$\underline{H}$N), 4.59 (0.5H, m, NC$\underline{H}_A$CH$_B$), 4.39 (0.5H, m, NC$\underline{H}_A$CH$_B$), 3.97-3.85 (4H, m, C$\underline{H}_2$OC$\underline{H}_2$), 3.20 (1H, m, NCH$_A$C$\underline{H}_B$), 2.89 (3H, s, C$\underline{H}_3$SO$_3^-$), 2.89-2.72 (2H, m, CC$\underline{H}_2$CH$_2$N), 2.23-2.07 (3H, m, C$\underline{H}$(CH$_3$)$_2$, OCH$_2$C$\underline{H}_2$), 1.16 (3H, d, J 6.4 Hz, C$\underline{H}_3$) and 1.06-0.96 (3H, m, C$\underline{H}_3$).

(3S)-Tetrahydrofuran-3-yl (4S)-4-isopropyl-1,4,6,7-tetrahydro-5H-imidazo[4,5-c]pyridine-5-carboxylate Sulfate (3S)-Tetrahydrofuran-3-yl (4S)-4-isopropyl-1,4,6,7-tetrahydro-5H-imidazo[4,5-c]-pyridine-5-carboxylate free base (440.4 mg, 1.6 mmol) was dissolved in IPAc (5 vol; 2.20 mL). The clear solution was heated to 40° C. and maintained at this temperature for 30 min. H$_2$SO$_4$ (1M solution in THF, 1 equivalent, 1.6 mL) was then added with gentle stirring, which caused precipitation of a white solid. The suspension was set to cool to 5° C. at 1° C./min and maintained at this temperature for 20 h. The solid was filtered by suction and dried under vacuum at room temperature overnight. (3S)-Tetrahydrofuran-3-yl (4S)-4-isopropyl-1,4,6,7-tetrahydro-5H-imidazo[4,5-c]pyridine-5-carboxylate sulphate salt was obtained with a 65% yield as a white solid. HPLC purity 99.3%. Melting point: 106° C. $^1$H NMR (400 MHz, CDCl$_3$): δ$_H$ 13.70 (1H, br, $\underline{H}$SO$_4^-$), 9.05 (1H, m, NHC$\underline{H}$NH$^+$), 5.28 (1H, m, OC$\underline{H}$), 4.95 (0.5H, d, J 8.4 Hz, CC$\underline{H}$N), 4.86 (0.5H, d, J 7.6 Hz, CC$\underline{H}$N), 4.55 (0.5H, m, NC$\underline{H}_A$CH$_B$), 4.35 (0.5H, m, NC$\underline{H}_A$CH$_B$), 3.95-3.74 (4H, m, C$\underline{H}_2$OC$\underline{H}_2$), 3.15 (1H, m, NCH$_A$CH$_B$), 2.78-2.67 (2H, m, CCH$_2$CH$_2$N), 2.21-1.99 (3H, m, CH(CH$_3$)$_2$, OCH$_2$CH$_2$), 1.09 (3H, d, CH$_3$) and 0.94-0.81 (3H, m, CH$_3$).

TABLE 2

Summary properties of (3S)-Tetrahydrofuran-3-yl (4S)-4-isopropyl-1,4,6,7-tetrahydro-5H-imidazo[4,5-c]pyridine-5-carboxylate free base and hydrochloride, phosphate, sulfate and mesylate salts

| Sample | Form | MP | Hygroscopicity |
|---|---|---|---|
| Free base | Amorphous gum | — | Deliquesced at 25° C./60% RH in <24 h |
| Hydrochloride salt | Crystalline solid | 168° C. | Deliquesced at 40° C./75% RH in <24 h |
| Phosphate salt | Crystalline solid | ND | Deliquesced at 40° C./75% RH in <24 h |
| Sulfate salt (.1.5H$_2$O) | Crystalline solid | 106° C. | No change at 40° C./75% RH for up to 7 days |
| Mesylate salt | Crystalline solid | 189° C. | Deliquesced at 40° C./75% RH after 3 days |

Stability/Hygroscopicity During Long Term Storage (3S)-Tetrahydrofuran-3-yl (4S)-4-isopropyl-1,4,6,7-tetrahydro-5H-imidazo[4,5-c]-pyridine-5-carboxylate mesylate was also assessed for stability and hygroscopicity when dispensed in 3 g aliquots in double LDPE liners, sealed with cable tie and placed, with a desiccant pouch into a foil bag, which was subsequently heat-sealed. The foil bag was then placed into an HDPE keg fitted with an HDPE lid. These conditions mirror typical GMP level storage conditions. Stability was assessed by HPLC and hygroscopicity was assessed by Karl Fisher (KF) titration. (3S)-Tetrahydrofuran-3-yl (4S)-4-isopropyl-1,4,6,7-tetrahydro-5H-imidazo[4,5-c]pyridine-5-carboxylate mesylate degraded by only 0.1% with no water uptake over 3 years at 25° C./60% RH, and by only 0.1% with only 0.1% water uptake after 6 months at 40° C./75% RH.

The invention claimed is:

1. A compound selected from:
   (3 S)-Tetrahydrofuran-3-yl (4S)-4-isopropyl-1,4,6,7-tetrahydro-5H-imidazo[4,5-c]pyridine-5-carboxylate mesylate having a melting point of 189° C., and
   (3 S)-Tetrahydrofuran-3-yl (4S)-4-isopropyl-1,4,6,7-tetrahydro-5H-imidazo[4,5-c]pyridine-5-carboxylate sulfate 1.5H$_2$O having a melting point of 106° C.

2. A pharmaceutical composition comprising:
   the compound according to claim 1, and
   one or more suitable excipients.

3. The compound according to claim 1, which is (3 S)-Tetrahydrofuran-3-yl (4S)-4-isopropyl-1,4,6,7-tetrahydro-5H-imidazo[4,5-c]pyridine-5-carboxylate mesylate having a melting point of 189° C.

4. The compound according to claim 3 having a purity of greater than 99.5%.

5. The compound according to claim 3 having an enantiomeric purity of greater than 99.5%.

6. The compound according to claim 1, which is (3 S)-Tetrahydrofuran-3-yl (4S)-4-isopropyl-1,4,6,7-tetrahydro-5H-imidazo[4,5-c]pyridine-5-carboxylate sulfate 1.5H$_2$O having a melting point of 106° C.

7. The compound according to claim 6 having a purity of greater than 99.3%.

8. The compound according to claim 6 having an enantiomeric purity of greater than 99.3%.

\* \* \* \* \*